(12) United States Patent
Hayes et al.

(10) Patent No.: US 8,597,712 B2
(45) Date of Patent: Dec. 3, 2013

(54) SOY BEVERAGE SUBSTANTIALLY FREE OF ISOFLAVONES AND METHOD OF PRODUCTION

(75) Inventors: Kirby Hayes, Broomfield, CO (US); Dennis Lane, Dexter, MI (US)

(73) Assignee: WhiteWave Services, Inc., Broomfield, CO (US)

( * ) Notice: Subject to any disclaimer, the term of this patent is extended or adjusted under 35 U.S.C. 154(b) by 510 days.

(21) Appl. No.: 12/891,279

(22) Filed: Sep. 27, 2010

(65) Prior Publication Data

US 2011/0076368 A1    Mar. 31, 2011

Related U.S. Application Data

(60) Provisional application No. 61/246,466, filed on Sep. 28, 2009.

(51) Int. Cl.
| | | |
|---|---|---|
| A23L 1/20 | (2006.01) |
| A23L 2/00 | (2006.01) |
| A23L 2/38 | (2006.01) |
| A23L 1/28 | (2006.01) |
| A23L 1/025 | (2006.01) |
| B02B 1/08 | (2006.01) |
| A23J 1/00 | (2006.01) |
| C07H 15/00 | (2006.01) |
| A61K 36/00 | (2006.01) |
| C07K 14/00 | (2006.01) |

(52) U.S. Cl.
USPC ........... 426/634; 426/590; 426/598; 426/489; 426/507; 426/656; 426/46; 426/238; 536/8; 530/370; 530/378

(58) Field of Classification Search
USPC ........... 426/364, 590, 598, 489, 46, 634, 507, 426/656, 238, 490, 271; 530/370, 378; 536/8
See application file for complete search history.

(56) References Cited

U.S. PATENT DOCUMENTS 3,809,771 A * 5/1974 Mustakas .................... 426/598
4,091,120 A    5/1978 Goodnight, Jr. et al.
(Continued)

FOREIGN PATENT DOCUMENTS

CN    101503469      8/2009
EP    0426998 A2    10/1990
(Continued)

OTHER PUBLICATIONS

Fukui et al., "Isoflavone-Free Soy Protein Prepared by Column Chromatography Reduces Plasma Cholesterol in Rats," Journal of Agricultural and Food Chemistry, 50, pp. 5717-5721, 2002.
(Continued)

*Primary Examiner* — Rena Dye
*Assistant Examiner* — Lela S Williams
(74) *Attorney, Agent, or Firm* — Baker Botts L.L.P.

(57) ABSTRACT

A method for removing isoflavones from a soy-based beverage is disclosed. The method includes processing a soy base by subjecting ground or milled soy beans to one or more of sonic vibration and ultrahigh pressure homogenization. The soy base is separated, using centrifugation, into a lipid phase substantially free from isoflavones and a serum phase containing isoflavones. One or more isoflavones are separated from the serum phase. The serum phase is mixed with the lipid phase.

10 Claims, 1 Drawing Sheet

(56) References Cited

U.S. PATENT DOCUMENTS

| | | | |
|---|---|---|---|
| 4,428,876 A * | 1/1984 | Iwamura | 530/370 |
| 4,997,489 A | 3/1991 | Rabinowitz | |
| 5,141,746 A | 8/1992 | Fleury et al. | |
| 5,679,806 A | 10/1997 | Zheng et al. | |
| 6,228,993 B1 | 5/2001 | Konwinski | |
| 7,037,547 B2 | 5/2006 | Akashe et al. | |
| 7,090,885 B2 | 8/2006 | Singh | |
| 7,323,200 B2 | 1/2008 | Chmura et al. | |
| 2005/0085632 A1 | 4/2005 | Johns et al. | 536/8 |
| 2005/0123662 A1 | 6/2005 | Wanezaki et al. | |

FOREIGN PATENT DOCUMENTS

| | | | |
|---|---|---|---|
| EP | 0 795 553 | | 9/1997 |
| EP | 1 166 643 | | 6/2000 |
| WO | WO 2005/020714 | | 3/2005 |
| WO | WO 2005094604 | * | 10/2005 |
| WO | WO 2008/070940 | | 6/2008 |

OTHER PUBLICATIONS

Chen et al., "Isoflavones in Soy Infant Formula: A Review of Evidence for Endocrine and Other Activity in Infants," Annu. Rev. Nutr., pp. 33-54 plus 2 contents pages, 2004.

Extended European search report; Application No./Patent No. 10181316.0-1221, Jan. 19, 2011.

* cited by examiner

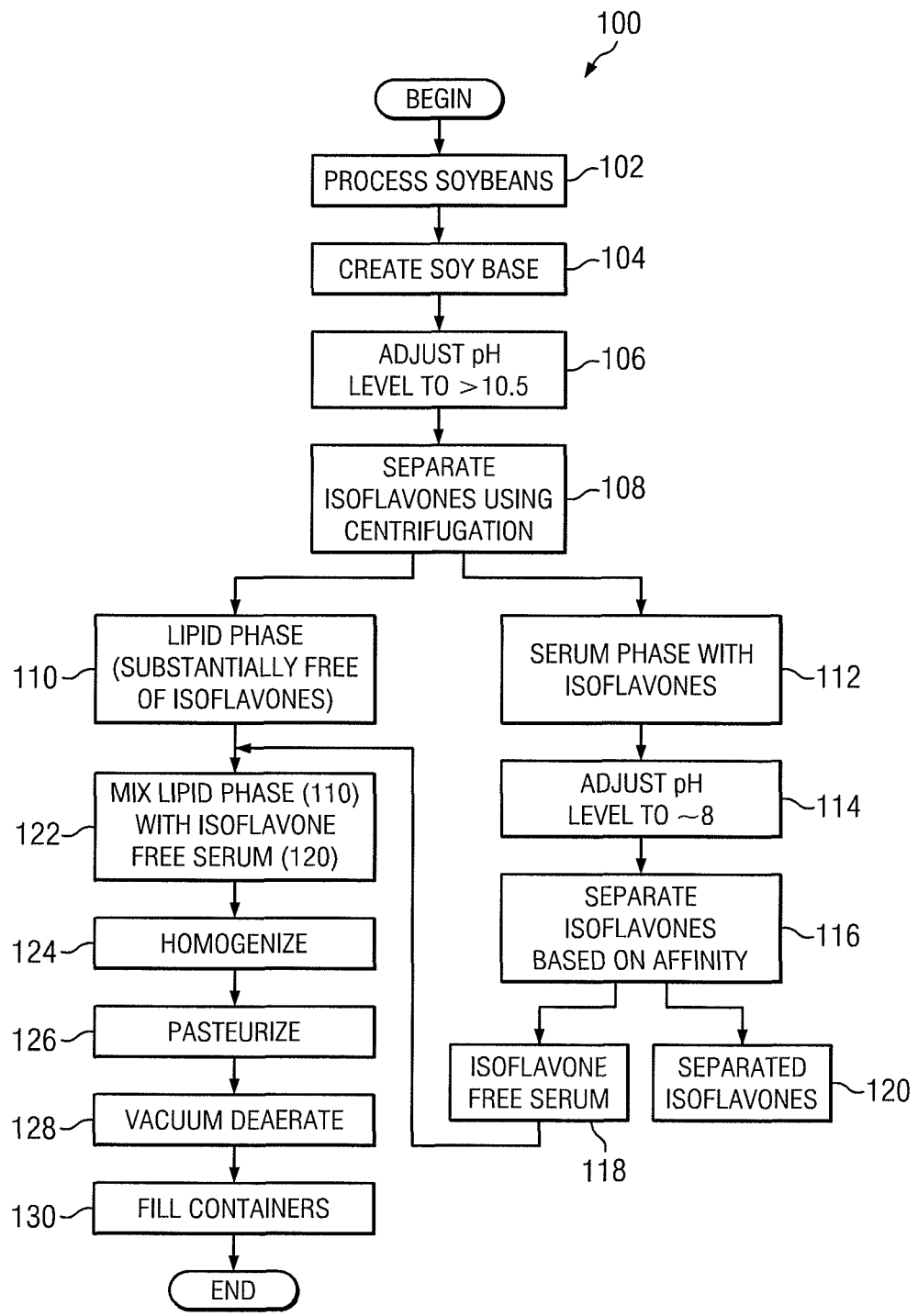

SOY BEVERAGE SUBSTANTIALLY FREE OF ISOFLAVONES AND METHOD OF PRODUCTION

RELATED APPLICATION

This application claims priority to U.S. Provisional Application No. 61/246,466 filed Sep. 28, 2009.

TECHNICAL FIELD

This disclosure relates generally to beverages, and more specifically to a soy beverage substantially free of isoflavones and methods of producing the same.

BACKGROUND

Soy and soy-derived ingredients are used in a variety of products for human consumption. For example, soy may be used to produce non-dairy milk. Soy thus provides an alternative to people who do not consume dairy products for a variety of reasons, including reasons related to digestion, allergies, lifestyle, or taste. Isoflavones are naturally occurring phytochemicals in soybeans. Consumption of isoflavones (e.g., genistein) has been associated by some with numerous health benefits including, for example, cardiovascular health and mitigation of cancer risks. However, some people avoid isoflavone consumption for a variety of reasons.

SUMMARY OF EXAMPLE EMBODIMENTS

In various embodiments, the teachings of the present disclosure may allow for stable, non-dairy, soy-based beverage that may be substantially or entirely free of isoflavones. In accordance with a particular embodiment, a method for removing isoflavones from a soy-based beverage is disclosed. The method includes processing a soy base by subjecting ground or milled soy beans to one or more of sonic vibration and ultrahigh pressure homogenization. The soy base is separated, using centrifugation, into a lipid phase substantially free from isoflavones and a serum phase containing isoflavones. One or more isoflavones are separated from the serum phase. The serum phase is mixed with the lipid phase.

Technical advantages of particular embodiments of the present disclosure include creating a stable, non-dairy, soy-based beverage that may be substantially or entirely free of isoflavones. In particular embodiments, isoflavones may be removed from a soy-based beverage with or without the use of isolated or concentrated soy protein. Particular embodiments may provide enhanced quality control while reducing product variation with regards to isoflavone removal. Further technical advantages of particular embodiments include the production of a beverage with extended shelf life, along with a desirable flavor and mouthfeel. The term "mouthfeel" as used herein generally refers to the sensation of a product in the mouth of a consumer, which sensation in some cases may be caused by the product's physical and/or chemical interaction in the mouth.

Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present invention and for further features and advantages thereof, reference is now made to the following description taken in conjunction with the accompanying drawings, in which:

FIG. 1 is a flow diagram illustrating a method of making a soy-based beverage that may be substantially or entirely free of isoflavones according to an example embodiment.

DETAILED DESCRIPTION

In various embodiments, the teachings of the present disclosure may allow for a stable, non-dairy, soy-based beverage that may be substantially or entirely free of isoflavones (e.g., genistein). Additionally, particular embodiments include the production of a substantially isoflavone-free, non-dairy, beverage with extended shelf life, along with a desirable flavor and a mouthfeel similar to dairy milk.

FIG. 1 is a flow diagram 100 illustrating a method of making a soy-based beverage that may be substantially or entirely free of isoflavones according to an example embodiment. The method begins at step 102 by processing soybeans. In a particular embodiment, the soy beans may be processed by grinding and/or milling the soybeans. At least part of the grinding and/or milling may be performed while submersing all or a portion of the soybeans in water heated to a temperature within the range of approximately 70 to 90 degrees Celsius (e.g., 80 degrees Celsius). During the grinding/milling process of certain embodiments, the pH may be controlled to a desired level at least in part by adding one or more ingredients. In particular embodiments, one or more of the following pH-controlling ingredients may be added: sodium hydroxide (NaOH); sodium carbonate ($Na_2CO_3$); sodium bicarbonate ($NaHCO_3$); potassium hydroxide (KOH); potassium carbonate ($K_2CO_3$); potassium bicarbonate ($KHCO_3$); calcium hydroxide ($Ca(OH)_2$); calcium carbonate ($CaCO_3$); calcium bicarbonate ($Ca(HCO_3)_2$); and/or any other suitable pH-controlling ingredient. Particular pH-controlling ingredients may also provide various health benefits (e.g., sources of sodium, potassium, calcium, etc.). According to one embodiment, a pH value within the range of approximately pH 7.8 to pH 10 (e.g., an average or target value of 9) may be maintained during the processing performed in step 102.

In step 104, the processed soy beans are converted to a soy base. In a particular embodiment, the processed soy beans may be subjected to sonication and/or to ultrahigh pressure homogenization. According to one embodiment, sonication may be performed, for example, for approximately 0.01 to 30 minutes at a frequency within the range of approximately 18 to 40 kilohertz (kHz) and a power within the range of approximately 0.5 to 16 kilowatts (kW); however, any suitable sonication parameters may be used. In certain embodiments, ultrahigh pressure homogenization may be performed, in addition to or in lieu of sonication, using one or more target pressures within the range of 2,000 to 60,000 pounds per square inch gauge (psig); however, any suitable homogenization process may be used. Various embodiments that use both sonication and ultra high pressure homogenization may enhance the degree to which isoflavones are removed. Additionally, various embodiments that use both sonication and ultra high pressure homogenization may enhance the mouthfeel of the final product. The process of converting the processed soy beans to a soy base in step 104 may result in subjecting the soy base to elevated temperatures and releasing isoflavones from the food matrix (e.g., protein and pectin).

In step 106, the pH level of the soy base may be adjusted. In a particular embodiment, the pH level of the soy base may be adjusted by the addition of one or more ingredients. In certain embodiments, for example, one or more of the following pH-controlling ingredients may be added: sodium hydroxide (NaOH); sodium carbonate ($Na_2CO_3$); sodium bicarbonate ($NaHCO_3$); potassium hydroxide (KOH); potassium carbonate ($K_2CO_3$); potassium bicarbonate ($KHCO_3$); calcium hydroxide ($Ca(OH)_2$); calcium carbonate ($CaCO_3$); calcium bicarbonate ($Ca(HCO_3)_2$); and/or any other suitable pH-controlling ingredient. Particular pH-controlling ingredients may also provide various health benefits (e.g., sources of sodium, potassium, calcium, etc.). According to one embodiment, the pH may be adjusted to approximately pH 10.5 or greater; however, the pH level may be adjusted to any suitable value or may not be adjusted at all. In certain embodiments, the soy base may be subjected to homogenization prior to adjusting the pH level, which in some cases may be the ultrahigh homogenization optionally performed in step 104 or which may be an alternative or additional homogenization process at a pressure less than or equal to approximately 2000 psig.

In step 108, the pH-adjusted soy base may be subjected to centrifugal separation (e.g., using approximately 2500×g). The centrifugal separation may, for example, separate components of the soy base according to density. In a particular embodiment, centrifuging the pH-adjusted soy base may create a lipid phase with low levels of isoflavones and a serum phase rich in isoflavones, as shown in blocks 110 and 112, respectively. Although this example uses centrifugal separation, any suitable separation technique may be used (e.g., affinity-based separation).

In step 114, the pH level of the isoflavone rich serum phase 112 may be adjusted to a value of approximately pH 7 to pH 9 (e.g., pH 8); however, any suitable pH level may be used. In a particular embodiment, the pH level may be reduced to a target range or value using an organic acid (e.g., ascorbic).

In step 116, isoflavones may be separated from serum 112. According to one embodiment, the separation of isoflavones from serum may be based at least partially on affinity separation. In a particular embodiment, for example, serum 112 may be forced through one or more hydrophobic resin membranes capable of filtering out and collecting the isoflavones. Serum 112 may thus be separated by filtration into a substantially isoflavone-free portion (block 120) and a portion containing isoflavones (block 122). In an alternative embodiment, a hydrophobic resin may be mixed with serum 112 such that the isoflavones become bound to resin beads; and the beads containing the isoflavones (block 122) may be separated from the substantially isoflavone free serum (block 120) by filtration. Particular embodiments may use a combination of separation techniques (e.g., the use of resin beads in addition to separation through the use of one or more resin membranes). Although certain example embodiments disclosed herein use affinity-based separation, any suitable separation technique may be used (e.g., centrifugal separation).

In step 124, the serum may be mixed with the lipid phase 110 to yield a soy-based product substantially or entirely free of isoflavones. Any suitable hydrophobic resin or combinations of resins may be used to form a resin membrane and/or resin beads including, for example, styrene, divinylbenzene, and/or other suitable hydrophobic resin capable of binding the isoflavones to the resin. In step 122, the serum may be mixed with the lipid phase 110 to yield a product substantially or entirely free of isoflavones.

In particular embodiments, the product may be homogenized, pasteurized, vacuum deaerated (e.g., −24.5 to 0 inches of Mercury or some other suitable range), and filled into containers in steps 124, 126, 128, and 130, respectively. For example, the product may be homogenized in step 124 using a pressure within the range of approximately 200 to 60,000 psig; however, any suitable homogenization process may be used. Ultra pasteurization may be effected in step 126 using a temperature of approximately 125 degrees Celsius for approximately 4 to 20 seconds; however, any suitable ultra pasteurization process may be used.

Thus, in particular embodiments, isoflavones may be removed from a soy-based beverage without necessarily using isolated or concentrated soy protein. Particular embodiments may provide enhanced quality control while reducing product variation with regards to isoflavone removal from a soy-based beverage. Further technical advantages of particular embodiments include the production of a beverage with extended shelf life, along with a desirable flavor and mouthfeel.

The components of the systems and apparatuses disclosed herein may be integrated or separated. Moreover, the operations of the systems and apparatuses may be performed by more, fewer, or other components. The methods may include more, fewer, or other steps. For example, in various embodiments, some or all of the homogenization discussed with reference to step 106 may alternatively be performed in step 104. Additionally, steps may be performed in any suitable order.

To aid the Patent Office, and any readers of any patent issued on this application in interpreting the claims appended hereto, applicants wish to note that they do not intend any of the appended claims to invoke paragraph 6 of 35 U.S.C. §112 as it exists on the date of filing hereof unless the words "means for" or "step for" are explicitly used in the particular claim.

Although the present disclosure has been described above in connection with several embodiments, a myriad of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims. For example, although the present disclosure has been described in the context of mass production, the teachings of the present disclosure may be applied on a smaller scale.

What is claimed is:

1. A method for removing isoflavones from a soy base, the method comprising:
    subjecting a mixture comprising water and soy beans to one or more of a grinding process and a milling process;
    maintaining the pH of the mixture comprising water and soy beans to a pH level of approximately pH 7,8 to pH 10, wherein the pH is maintained at least in part by blending one or more pH-controlling ingredients with the mixture;
    converting the mixture to the soy base by subjecting the mixture to one or more processes selected from the group consisting of sonic vibration and ultrahigh pressure homogenization;
    adjusting the pH level of the soy base to approximately pH 10.5 or greater;
    separating the soy base, using centrifugation, into a lipid phase substantially free from isoflavones and a serum phase containing isoflavones;
    adjusting the pH level of the serum phase to a level within the range of approximately pH 7 to pH 9;
    separating isoflavones from the serum phase; and
    mixing the lipid phase with the separated serum phase.

2. The method of claim 1, wherein the ultrahigh pressure homogenization comprises a homogenization pressure of approximately 2,000 pounds per square inch gauge (psig) or greater.

3. The method of claim 1, wherein the sonic vibration comprises a frequency of approximately 18 to 40 kilohertz (kHz).

4. The method of claim 1, wherein the one or more pH-controlling ingredients blended with the mixture is selected from the group consisting of:
   sodium hydroxide (NaOH);
   sodium carbonate ($Na_2CO_3$);
   sodium bicarbonate ($NaHCO_3$);
   potassium hydroxide (KOH);
   potassium carbonate ($K_2CO_3$);
   potassium bicarbonate ($KHCO_3$);
   calcium hydroxide ($Ca(OH)_2$);
   calcium carbonate ($CaCO_3$); and
   calcium bicarbonate ($Ca(HCO_3)_2$).

5. The method of claim 1, wherein the pH level of the soy base is adjusted to approximately pH 10.5 or greater at least in part by mixing one or more ingredients with the soy base selected from the group consisting of:
   sodium hydroxide (NaOH);
   sodium carbonate ($Na_2CO_3$);
   sodium bicarbonate ($NaHCO_3$);
   potassium hydroxide (KOH);
   potassium carbonate ($K_2CO_3$);
   potassium bicarbonate ($KHCO_3$);
   calcium hydroxide ($Ca(OH)_2$);
   calcium carbonate ($CaCO_3$); and
   calcium bicarbonate ($Ca(HCO_3)_2$).

6. The method of claim 1, wherein the pH level of the serum phase is adjusted to a level within the range of approximately pH 7 to pH 9 by mixing an organic acid. with the soy base.

7. The method of claim 6, wherein the organic acid is ascorbic.

8. The method of claim 1, wherein separating isoflavones from the serum phase comprises separating isoflavones from the serum phase using one or more hydrophobic resin membranes.

9. The method of claim 1, wherein separating isoflavones from the serum phase comprises separating isoflavones from the serum phase using a plurality of hydrophobic resin beads.

10. The method of claim 1, further comprising simultaneously performing:
   the subjecting the mixture comprising water and soy beans to one or more of the grinding process and the milling process; and
   the maintaining the pH of the mixture comprising water and soy beans to the pH level of approximately pH 7.8 to pH 10.

* * * * *